United States Patent [19]

Cassandrini et al.

[11] 4,086,207
[45] Apr. 25, 1978

[54] POLYUREA COMPOUNDS WHICH IMPROVE THE LIGHT STABILITY OF POLYMERS

[75] Inventors: Paolo Cassandrini, Bologna; Antonio Tozzi, Sasso Marconi, both of Italy

[73] Assignee: Chimosa Chimica Organica S.p.A., Marconi, Italy

[21] Appl. No.: 699,161

[22] Filed: Jun. 23, 1976

[30] Foreign Application Priority Data

Nov. 18, 1975 Italy ................... 52254/75

[51] Int. Cl.$^2$ .................. C08K 5/34; C08G 18/32; C07D 211/98
[52] U.S. Cl. .................. 260/45.8 N; 260/77.5 C; 260/77.5 CH; 260/293.63; 260/293.69; 260/293.86; 260/858
[58] Field of Search ............ 260/45.8 N, 77.5 C, 260/77.5 CH, 293.63, 293.86, 293.69, 858

[56] References Cited

U.S. PATENT DOCUMENTS

| | | | |
|---|---|---|---|
| 2,816,879 | 12/1957 | Wittbecker | 260/77.5 C |
| 3,352,875 | 11/1967 | McGill | 260/293.63 |
| 3,684,765 | 8/1972 | Matsui et al. | 260/45.8 N |
| 3,904,581 | 9/1975 | Murayama et al. | 260/45.8 N |
| 3,907,803 | 9/1975 | Ramey et al. | 260/293.86 |
| 3,965,072 | 6/1976 | Markiewitz | 260/77.5 C |

*Primary Examiner*—H.S. Cockeram
*Attorney, Agent, or Firm*—Cushman, Darby & Cushman

[57] ABSTRACT

Novel polyurea compounds having the general formula

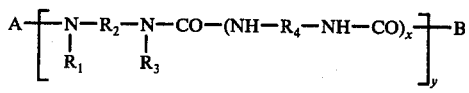

where $R_1$ is hydrogen, alkyl, cycloalkyl, aryl, substituted aryl, aralkyl, or a piperidine radical of the formula

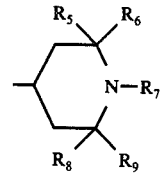

where $R_5$, $R_6$, $R_8$ and $R_9$ are alkyl and $R_7$ is hydrogen, oxygen, alkyl, alkenyl, alkinyl or aralkyl, $R_2$ is alkylene, cycloalkylene, arylene or aralkylene, $R_3$ is a piperidine radical as set forth above, $R_4$ is alkylene, cycloalkylene, arylene or aralkylene, X is zero or one, $y$ is an integer from 2 to 200 and A and B each represent a terminal group. In some of the $y$ units and in B the

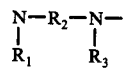

can be replaced in part by

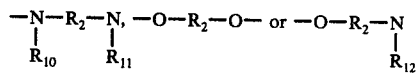

where $R_{10}$, $R_{11}$ and $R_{12}$ are hydrogen, alkyl, cycloalkyl, aryl, aralkyl or $R_{10}$ and $R_{11}$, are linked together so that

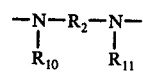

forms a 6 to 8 member heterocyclic ring are produced by reacting a diamine with carbonyl chloride or a diisocyanate. The compounds are valuable light stabilizers for synthetic polymers, particularly polypropylene and polyethelene.

23 Claims, No Drawings

POLYUREA COMPOUNDS WHICH IMPROVE THE LIGHT STABILITY OF POLYMERS

BACKGROUND OF THE INVENTION

1. Field of the Invention

The present invention relates to novel polyurea compounds which are useful for improviding the stability to light, heat and oxidation of polymeric substances.

2. Description of the Prior Art

It is known that synthetic polymers are liable to undergo a severe deterioration of their physical and chemical properties when they are exposed to sunlight or other ultraviolet light source.

In order to improve the stability to light of said synthetic polymers, various stabilizers have been proposed, some of which have found a wide commercial acceptance in the field, such as some benzophenones, benzotriazoles, aromatic salicylates, α-cyanoacrylic acid esters, organo-tin compounds and the like, which, although having a certain efficiency level, are not successful to solve the problem completely, so that a need of more efficient stabilizers is very much felt in the field.

SUMMARY

An object of the invention is to provide new compounds consisting of urea polymers having the following general formula:

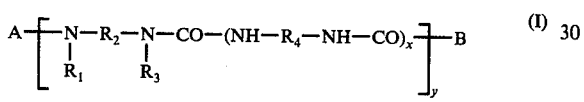

in which:

$R_1$ is hydrogen, a straight or branched chain alkyl having 1 to 18 C atoms, a cycloalkyl having 5 to 18 C atoms, a substituted or non-substituted aryl having 6 to 18 C atoms, aralkyl having 7 to 18 C atoms, and a piperidine radical of the formula:

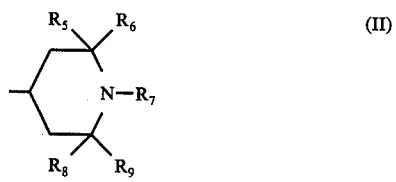

wherein each of $R_5$, $R_6$, $R_8$ and $R_9$ is a $C_1$ to $C_6$ alkyl, and $R_7$ is hydrogen, oxygen, a $C_1$ to $C_{18}$ straight or branched chain alkyl, a $C_2$ to $C_{18}$ alkenyl or alkinyl, and $C_7$ to $C_{18}$ aralkyl;

$R_2$ is a $C_2$ to $C_{18}$ straight or branched chain alkylene, a $C_5$ to $C_{18}$ cycloalkylene, a $C_6$ to $C_{18}$ arylene, and a $C_7$ to $C_{18}$ aralkylene;

$R_3$ is a piperidine radical of the formula (II);

$R_4$ is a $C_2$ to $C_{18}$ straight or branched chain alkylene, a $C_5$ to $C_{18}$ cycloalkylene, a $C_6$ to $C_{18}$ arylene, and a $C_7$ to $C_{18}$ aralkylene;

$x$ is either 0 or 1;

$y$ is an integer from 2 to 200;

A and B represent the terminal groups.

By the term "terminal groups" it is meant the terminal groups of a molecule of formula (I) resulting from the polymerization reaction, which generally are a residue of functional groups. The nature of said residue depends on the reaction conditions, the nature and amount of the reactants used in the reaction, for example, as it is known to one skilled in the art. Said residue is preferably H for A and

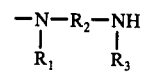

for B, in that it is preferred to use an excess of diamine compound in the reaction for controlling the molecular weight, as will be more fully described later.

In some of the $y$ units and in group B, the radical

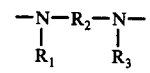

may be partially substituted with one of the radicals

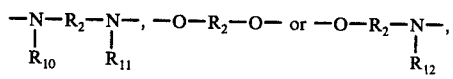

wherein $R_2$ is as above indicated, $R_{10}$, $R_{11}$, $R_{12}$, similar or different, are hydrogen, a $C_1$ to $C_{18}$ straight or branched chain alkyl, $C_5$ to $C_{18}$ cycloalkyl, a $C_6$ to $C_{18}$ aryl, a $C_7$ to $C_{18}$ aralkyl, or $R_{10}$ and $R_{11}$ are linked together so that the group

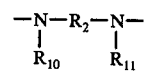

forms a 6 to 8 member heterocyclic ring containing 2 nitrogen atoms.

An additional object of the invention is to provide a method for the preparation of the above compounds of formula (I).

A further object of the invention is to provide new stabilizers for synthetic polymers for improving their stability to light, heat and oxidation.

A further object of the invention is to provide a composition of material comprising a synthetic polymer and an amount of a stabilizer of formula (I) effective to improve the weather resistance thereof, as well as additional optional additives.

THE DETAILED DESCRIPTION

In accordance with this invention, in a urea polymer of formula (I), the following preferred embodiments are intended for the various substituent groups: $R_1$ represents hydrogen, methyl, ethyl, n-butyl, isobutyl, n-octyl, n-dodecyl, cyclohexyl, phenyl, benzyl, 2,2,6,6-tetramethyl-4-piperidyl, 1,2,2,6,6-pentamethyl-4-piperidyl, 1-propyl-2,2,6,6-tetramethyl-4-piperidyl. Preferred examples of $R_2$ are ethylene, 1,2-propylene, trimethylene, hexamethylene, decamethylene, 1,4-cyclohexylene, 1,4-bis-(methylene)cyclohexylene, 4,4'-methylenedicyclohexylene, o-, m-, p-phenylene, o-, m-, p-xylylene.

Representatives of $R_3$ are 2,2,6,6-tetramethyl-4-piperidyl, 1,2,2,6,6-pentamethyl-4-piperidyl, 1-propyl-2,2,6,6-tetramethyl-4-piperidyl.

Representatives of $R_4$ are hexamethylene, 2,2,4-trimethylhexamethylene, 2,4,4-trimethylhexamethylene, m-toluylene, 4,4'-methylenediphenylene.

More particularly, preferred embodiments for the radical
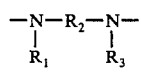
are:
PREPARATION
When in formula (I), $x$ is zero, a compound according to formula (I) can be prepared by reacting carbonyl chloride with a diamine of the following formula (III):
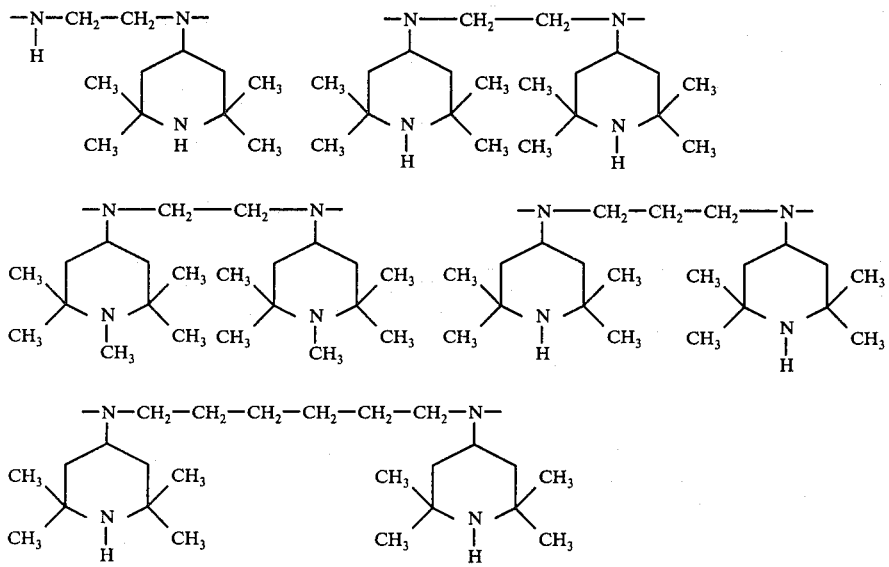
Representatives of $R_4$ are
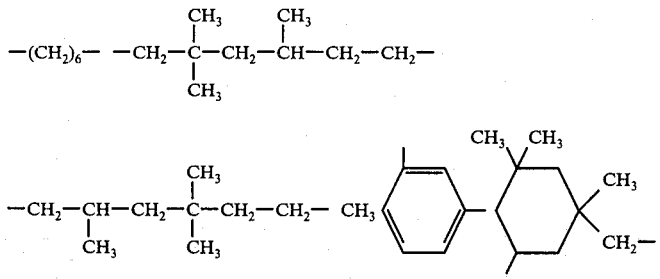
Representatives of radical
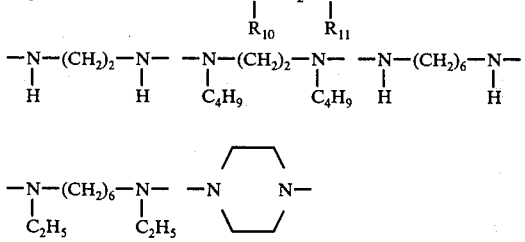
Examples of radical $-OR_2O-$ are:
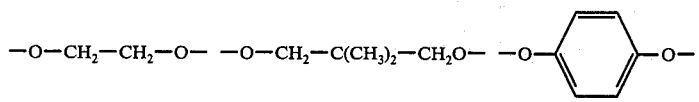
Examples of radical $-O-R_2-N(R_{12})-$ are:
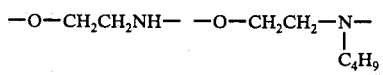

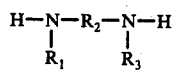 (III)

The reaction is carried out in an inert solvent, such as methylene chloride, chloroform, carbon tetrachloride, petroleum ether, hexane, cyclohexane, benzene, toluene, in the presence of suitable organic or inorganic bases for fixing hydrogen chloride.

Preferred examples of base useful to said purpose are pyridine, triethylamine, sodium hydroxide or carbonate, potassium hydroxide or carbonate.

When in formula (I), $x$ is one, a compound according to formula (I) can be prepared by reacting a diisocyanate of the following formula (IV):

 (IV)

with a diamine of formula (III), carrying out the reaction preferably in the presence of an inert solvent such as petroleum ether, hexane, cyclohexane, benzene.

The molar ratio between reactants of formula (III) and $COCl_2$ or between reactants of formula (III) and reactants of formula (IV) may be in a range from 1:1 to 1.5:1, preferably from 1:1 to 1.2:1.

It is further possible in a compound of formula (I) to partially replace a diamine of formula (III) by a diamine of the following formula (V):

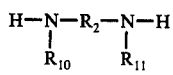 (V)

or a glycol or a diphenol of formula (VI)

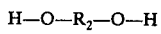 (VI)

or an aminoalcohol of formula (VII)

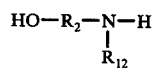 (VIII)

The molar amount of a bifunctional compound of formula (V), (VI) or (VII) can be in a range from 0 to 2 moles per mole of diamine of formula (III), preferably from 0 to 1 mole.

In the following examples given for an illustrative and not limitative purpose, several syntheses of polyurea compounds of formula (I) are described.

EXAMPLE 1

To 36.95 g (0.105 moles) of 1,3-bis(2,2,6,6-tetramethyl-4-piperidylamino)-propane dissolved in 400 ml hexane, were added 16.8 g (0.1 mole) of hexamethylenediisocyanate at 10°-15° C.

The mixture was stirred for 1 hour at 10°-15° C, followed by 1 hour at 50° C. Then it was cooled and filtered.

A white powder of reduced viscosity (0.18 at 1% b.w. in chloroform at 25° C) was obtained.

EXAMPLE 2

To 37.18 g (0.11 moles) of 1,2-bis-(2,2,6,6-tetramethyl-4-piperidylamino)-ethane dissolved in 400 ml hexane were added 17.4 g (0.1 mole) of toluylene-2,4-diisocyanate at 10°-15° C.

The mixture was stirred for 1 hour at 10°-15° C, followed by 1 one hour at 60° C. Then it was cooled and filtered.

A white powder of reduced viscosity (0.12 at 1% b.w. in chloroform at 25° C) was obtained.

EXAMPLE 3

To 36.95 g (0.105 moles) of 1,3-bis(2,2,6,6-tetramethyl-4-piperidylamino)propane dissolved in 400 ml hexane were added 17.4 g (0.1 mole) of toluylene-2.4-diisocyanate at 10°-15° C.

The mixture was stirred for 1 hour at 10°-15° C, followed by one hour at 60° C. It was cooled and filtered.

A white powder of reduced viscosity (0.15 at 1% b.w. in chloroform at 25° C) was obtained.

EXAMPLE 4

To 37.18 g (0.11 moles) of 1,2-bis-(2,2,6,6-tetramethyl-4-piperidylamino)ethane dissolved in 400 ml octane were added 16.8 g (0.1 moles) of hexamethylenediisocyanate at 10°-15° C.

The mixture was stirred for 1 hour at 10°-15° C, followed by 1 hour at 80° C. Then it was cooled and filtered.

A white powder of reduced viscosity (0.16 at 1% b.w. in chloroform at 25° C) was obtained.

EXAMPLE 5

To 35.49 g (0.105 moles) of 1,2-bis-(2,2,6,6-tetramethyl-4-piperidylamino)ethane dissolved in 400 ml benzene were added 16.8 g (0.1 mole) of hexamethylenediisocyanate at 10°-15° C.

The mixture was stirred for 1 hour at 10°-15° C, followed by 30 minutes at 80° C. Then it was cooled and filtered.

A white powder of reduced viscosity (0.21 at 1% b.w. in chloroform at 25° C) was obtained.

EXAMPLE 6

To 41.37 g (0.105 moles) of 1,6-bis-(2,2,6,6-tetramethyl-4-piperidylamino)hexane dissolved in 400 ml hexane were added 16.8 g (0.1 mole) of hexamethylenediisocyanate at 10°-15° C.

The mixture was stirred for 1 hour at 10°-15° C, followed by 1 hour at 60° C. Then it was cooled and filtered.

A white powder of reduced viscosity (0.25 at 1% b.w. in chloroform at 25° C) was obtained.

EXAMPLE 7

To 25.3 g (0.075 moles) of 1,2-bis-(2,2,6,6-tetramethyl-4-piperidylamino)ethane and 3.6 g (0.025 moles) of 2,5-dimethyl-2,5-hexanediamine dissolved in 400 ml hexane were added 16.8 g (0.1 moles) of hexamethylene-diisocyanate at 10°-15° C.

The mixture was stirred for 1 hour at 10°-15° C, followed by 1 hour at 60° C. Then it was cooled and filtered.

A white powder of reduced viscosity (0.25 at 1% b.w. in isopropanol at 25° C) was obtained.

EXAMPLE 8

To 21.89 g (0.11 moles) of 2-(2,2,6,6-tetramethyl-4-piperidylamino)ethylamine dissolved in 400 ml hexane were added 16.8 g (0.1 mole) of hexamethylenediisocyanate at 10°-15° C.

The mixture was stirred for 1 hour at 10°–15° C, followed by 1 hour at 60° C. Then it was cooled and filtered.

A white powder of reduced viscosity (0.12 at 1% b.w. in isopropanol at 25° C) was obtained.

EXAMPLE 9

To a solution of 43.34 g (0.11 moles) of 1,6-bis-(2,2,6,6-tetramethyl-4-piperidyl-amino)hexane and 8 g (0.2 moles) of sodium hydroxide in 400 water was added a solution of 9.9 g (0.1 mole) of carbonyl chloride in 400 ml toluene, under vigorous stirring, keeping the temperature between 5° and 10° C.

The mixture was left standing for 1 hour at 5°–10° C, then heated to 80° C for one additional hour.

After removing the solvent, washing with water and drying, a white solid product of reduced viscosity (0.21 at 1% b.w. in chloroform at 25° C) was obtained.

EXAMPLE 10

To 35.49 g (0.105 moles) of 1,2-bis(2,2,6,6-tetramethyl-4-piperidylamino)ethane dissolved in 400 ml hexane were added 22.2 g (0.1 mole) of isophoronediisocyanate at 10°–15° C.

The mixture was stirred for 1 hour at 10°–15° C, followed by 1 hour at 50° C. Then it was cooled and filtered.

A white powder of reduced viscosity (0.16 at 1% b.w. in chloroform at 25° C) was obtained.

EXAMPLE 11

To 35.49 g (0.105 moles) of 1,2-bis(2,2,6,6-tetramethyl-4-piperidylamino)ethyl dissolved in 400 ml hexane were added 21 g (0.1 mole) of trimethyl-hexamethylenediisocyanate (a mixture of 2,2,4- and 2,4,4-trimethyl-hexamethylenediisocyanate isomers) at 10°–15° C.

The mixture was stirred for 1 hour at 10°–15° C, followed by 1 hour at 50° C. Then it was cooled and filtered.

A white powder of reduced viscosity (0.18 at 1% b.w. in chloroform at 25° C) was obtained.

EXAMPLE 12

To 27 g (0.08 moles) of 1,2-bis(2,2,6,6-tetramethyl-4-piperidylamino)ethane and 2.1 g (0.02 moles) of 2,2-dimethyl-1,3-propandiol dissolved in 400 ml benzene were added 16.8 g (0.1 mole) of hexamethylenediisocyanate at 10°–15° C.

The mixture was stirred for 1 hour at 10°–15° C and for 2 hours at 80° C. Then it was cooled and filtered.

A white powder of reduced viscosity (0.18 at 1% b.w. in chloroform at 25° C) was obtained.

Light Stabilization Tests

The polyurea compounds of formula (I) are useful and valuable agents for improving the stability to light, heat and oxidation of synthetic polymers such as, for example, high and low density polyethylene, polypropylene, ethylene-propylene copolymers, ethylene-vinylacetate copolymers, polybutadiene, polyisoprene, polystyrene, styrene-butadiene copolymers, acrylonitrile-butadiene-styrene copolymers, vinyl- and vinylidene chloride polymers and copolymers, polyacetals such as polyoxymethylene for example, polyesters such as polyethylene-terephthalate for example, polyamides such as nylon 66, nylon 6, nylon 12 for example, polyurethanes.

The compounds of Formula (I) can be employed in a mixture with the synthetic polymers in various proportions, depending on the polymer nature, final use and presence of additional additives.

Generally it is preferable to employ from 0.01 to 5% by weight of compounds of formula (I) referred to the polymer weight, more preferably from 0.1 to 1%.

The compounds of formula (I) can be included in a polymeric material composition by various procedures, such as dry mixing in the form of powder, or by a wet process in the form of a solution or slurry. In said operation the synthetic polymer can be employed in the form of powder, granulate, solution, slurry or emulsion.

The polymers stabilized by the products of formula (I) can be used for the manufacture of molded articles, films, tapes, fibers, monofilaments and the like.

A mixture of compounds of formula (I) and synthetic polymers can be optionally additioned with other additives, such as antioxidants, UV absorbers, nickel stabilizers, pigments, charges, plastifying agents, antistatic agents, flame retardants, lubricating agents, anticorrosive agents, metal inhibitors, and the like.

Particular examples of additives which can be employed in a mixture with the polyurea compounds of formula (I) are:

phenolic antioxidants, such as 2,6-ditert-butyl-p-cresol, 4,4'-thiobis-(3-methyl-6-tertbutylphenol), 1,1,3-tris-(2-methyl-4-hydroxy-5-tertbutylphenyl)butane, octadecyl-3-(3,5-ditertbutyl-4-hydroxyphenyl)propionate, pentaerythritol-tetra-(3,5-ditert-butyl-4-hydroxyphenyl)propionate, tris-(3,5-ditert-butyl-4-hydroxybenzyl)isocyanurate;

esters of thiodipropionic acid, such as di-n-dodecyl-thiodipropionate, di-n-octadecyl-thiodipropionate, aliphatic sulfides and disulfides, such as di-n-dodecyl-sulfide, di-n-octadecyl-sulfide, di-n-octadecyl-disulfide;

aliphatic, aromatic or aliphatic-aromatic phosphites and thiophosphites, such as tri-n-dodecyl-phosphite, tris-(n-nonylphenyl)phosphite, tri-n-dodecyl-trithiophosphite, phenyl-di-n-decylphosphite, di-n-octadecyl-pentaerythritoldiphosphite;

UV absorbers such as 2-hydroxy-4-octyloxybenzophenone, 2-hydroxy-4-n-dodecyloxybenzophenone, 2-(2'-hydroxy-3',5'-ditert-butylphenyl)-5-chlorobenzotriazole, 2-(2'-hydroxy-3',5'-di-tert-amylphenyl)benzotriazole, 2,4-ditertbutylphenyl-3,5-ditertbutyl-4-hydroxybenzoate, phenyl-salicylate, p-tertbutylphenyl-salicylate, 2,2'-dioctyloxy-5,5'-ditertbutyloxanilide, 2-ethoxy-5-tertbutyl-2'-ethyloxanilide;

nickel stabilizers such as Ni monoethyl-3,5-di-tertbutyl-4-hydroxybenzylphosphonate, butylamine-Ni 2,2'-thiobis-(4-tertoctylphenolate) complex, Ni 2,2'-thiobis-(4-tertoctylphenolphenolate), Ni dibutyldithiocarbamate, Ni 3,5-ditertbutyl-4-hydroxybenzoate, Ni complex of 2-hydroxy-4-n-octyloxybenzophenone;

organo-tin compounds, such as dibutyl-tin-maleate, dibutyl-tin-laurate, di-n-octyl-tin-maleate;

acrylic esters, such as ethyl-α-cyano-β,β-diphenylacrylate, methyl-α-cyano-β-methyl-4-methoxycinnamate;

metal salts of higher fat acids, such as calcium, barium, zinc, cadmium, lead, nickel stearates, calcium cadmium, barium, zinc laurates.

In the following several examples are described, in an illustrative and not limitative way, for illustrating the application of the compounds of formula (I) obtained in example 1–12, for the stabilization of synthetic polymers.

EXAMPLE 13

2.5 g of each of the compounds listed in table 1 below, dissolved in 100 ml chloroform, were mixed with 1000 g polypropylene (Moplen C, manufactured by Societa Montedison, Italy), 1 g n-octadecyl-3(3,5-ditert.butyl-4-hydroxy-phenyl)propionate and 1 g calcium stearate.

The solvent was removed in an oven under vacuum at a temperature of 50° C for 4 hours.

The dry mixture so obtained was then extruded at a temperature of 200° C and made into granules, wherefrom 0.2 mm thick plates were produced by diecasting at 200° C.

Said plates were exposed in a Xenotest 150 apparatus at a black panel temperature of 60° C and the increase in the content of carbonyl groups was periodically determined using the not exposed specimens for balancing the original polymer absorption. The time (T 0.1) required to have a $\Delta CO\% = 0.1$ at 5.85 um was then calculated.

As a comparison, a polymer plate was produced under the same conditions, but without addition of any light stabilizer, and another one with the addition of 2.5 g of 2-hydroxy-4-n-octyloxybenzophenone, a usual commercial stabilizer.

The results are referred in Table 1.

Table 1

| Stabilizer | T 0.1 (hours) |
| --- | --- |
| None | 260 |
| 2-hydroxy-4-n-octyloxybenzophenone | 900 |
| Compound of example 1 | 1420 |
| Compound of example 2 | 970 |
| Compound of example 3 | 950 |
| Compound of example 4 | 1480 |
| Compound of example 5 | 1310 |
| Compound of example 6 | 1250 |
| Compound of example 7 | 920 |
| Compound of example 8 | 1070 |
| Compound of example 9 | 1390 |
| Compound of example 10 | 1420 |
| Compound of example 11 | 1320 |
| Compound of example 12 | 1240 |

EXAMPLE 14

2 g of each of the compounds listed in table 2 below, dissolved in 100 ml chloroform, were mixed with 1000 g of high density polyethylene (Moplen RO, manufactured by Societa Montedison, Italy), 0.5 g of n-octadecyl-3(3,5-ditert.butyl-4-hydroxy-phenyl)propionate and 1 g of calcium stearate.

The solvent was removed in an oven under vacuum at a temperature of 50° C for 40 hours.

The dry mixture so obtained was then extruded at a temperature of 190° C and made into granules, wherefrom by die-casting at 200° C plates 0.2 mm thick were produced, said plates were exposed in a Xenotest 150 apparatus, as in example 13.

The time T 0.05 required to have $\Delta CO\% = 0.05$ at 5.85 μm was determined.

As a comparison, under the same conditions a polymer plate was produced without addition of any light stabilizer and another plate was produced with addition of 2 g of 2-hydroxy-4-n-octyloxybenzophenone.

The results are referred in table 2.

Table 2

| Stabilizer | T 0.05 (hours) |
| --- | --- |
| None | 320 |
| 2-hydroxy-4-n-octyloxybenzophenone | 1100 |
| Compound of example 1 | 2060 |
| Compound of example 2 | 1350 |

Table 2-continued

| Stabilizer | T 0.05 (hours) |
| --- | --- |
| Compound of example 3 | 1480 |
| Compound of example 4 | 2100 |
| Compound of example 5 | 1980 |
| Compound of example 6 | 1890 |
| Compound of example 7 | 1520 |
| Compound of example 8 | 1810 |
| Compound of example 9 | 2050 |
| Compound of example 10 | 2330 |
| Compound of example 11 | 1970 |
| Compound of example 12 | 1700 |

EXAMPLE 15

The polypropylene granules produced in example 13 were made into fibres under the following conditions:

Extruder temperature:250°-260° C
Die temperature:250° C
Stretching ratio:1:4
Multifilament count:1130/200 den The fibers were assembled on a white paperboard and exposed until brittleness in a xenotest 150 at a black panel temperature of 60° C.

As a comparison under the same conditions, polypropylene fibers were produced and treated without addition of any stabilizer, as well as with addition of 0.25% by weight of 2-hydroxy-4-n-octyloxybenzophenone.

The results obtained are referred in table 3.

Table 3

| Stabilizer | Time to brittleness (hours) |
| --- | --- |
| None | 110 |
| 2-hydroxy-4-n-octyloxybenzophenone | 670 |
| Compound of example 1 | 1190 |
| Compound of example 2 | 960 |
| Compound of example 3 | 910 |
| Compound of example 4 | 1270 |
| Compound of example 5 | 1200 |
| Compound of example 6 | 1180 |
| Compound of example 7 | 930 |
| Compound of example 8 | 950 |
| Compound of example 9 | 1210 |
| Compound of example 10 | 1350 |
| Compound of example 11 | 1100 |
| Compound of example 12 | 1040 |

From the test results, a considerable increase in the time required to induce a degradation in a polymer stabilized by the invention compounds can be observed with respect to the same polymer not stabilized. Furthermore, clearly improved effects induced by the invention compounds can be observed in comparison with a similar proportion of a prior art additive.

We claim:

1. A compound which either (1) has the formula

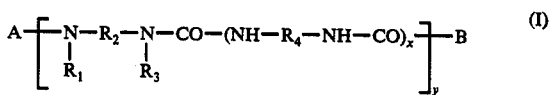

wherein:

$R_1$ is a member selected from hydrogen, straight and branched alkyl having 1 to 18 carbon atoms, cycloalkyl having 5 to 18 carbon atoms, aryl and substituted aryl having 6 to 18 carbon atoms, aralkyl having 7 to 18 carbon atoms, a piperidine radial having the formula:

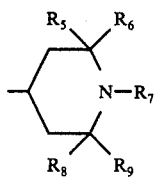 (II)

in which $R_5$, $R_6$, $R_8$ and $R_9$ are members individually selected from alkyl having 1 to 6 carbon atoms and $R_7$ is selected from hydrogen, oxygen, straight and branched chain alkyl having 1 to 18 carbon atoms, alkenyl and alkinyl having 2 to 18 carbon atoms, aralkyl having 7 to 18 carbon atoms;

$R_2$ is a member selected from straight and branched chain alkylene having 2 to 18 carbon atoms, cycloalkylene having 5 to 18 carbon atoms, arylene having 6 to 18 carbon atoms, aralkylene having 7 to 18 carbon atoms;

$R_3$ is a piperidine radical of formula (II);

$R_4$ is a member selected from straight and branched chain alkylene having 2 to 18 carbon atoms, cycloalkylene having 5 to 18 carbon atoms, arylene having 6 to 18 carbon atoms, aralkylene having 7 to 18 carbon atoms;

$x$ is either 0 or 1;

$y$ is an integer from 2 to 200;

A and B each represents a terminal group wherein A is H and B is

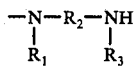

or (2) has the formula (I) in which a proportion of the $y$ units and the terminal group B has the radical

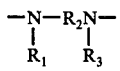

replaced by

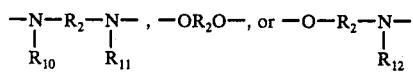

wherein $R_{10}$, $R_{11}$ and $R_{12}$ are hydrogen, alkyl having 1 to 18 carbon atoms, cycloalkyl having 5 to 18 carbon atoms, aryl having 6 to 18 carbon atoms, aralkyl having 7 to 18 carbon atoms, or $R_{10}$ and $R_{11}$ are linked together so that the group

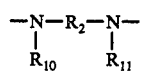

forms a heterocyclic ring having 6 to 8 inclusive members and which contains 2 nitrogen atoms; the proportion of $y$ units with a replaced radical resulting from using in the reaction not over 2 moles of an amine or hydroxyl reactant containing the replacing radicals

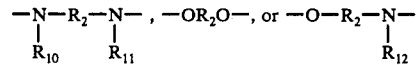

per mole of the amine reactant containing the radical

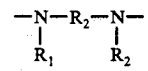

so that per one $y$ unit containing a radical

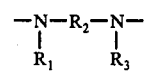

0 to 2 $y$ units having said radical replaced are present.

2. A compound according to claim 1 having the formula

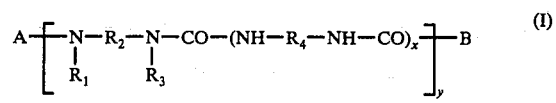 (I)

wherein:

$R_1$ is a member selected from hydrogen, straight and branched alkyl having 1 to 18 carbon atoms, cycloalkyl having 5 to 18 carbons atoms, aryl and substituted aryl having 6 to 18 carbon atoms, aralkyl having 7 to 18 carbon atoms, a piperidine radical having the formula

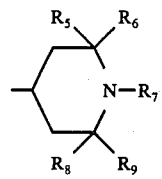 (II)

in which $R_5$, $R_6$, $R_8$ and $R_9$ are members individually selected from alkyl having 1 to 6 carbon atoms and $R_7$ is selected from hydrogen, oxygen, straight and branched chain alkyl having 1 to 18 carbon atoms, alkenyl and alkinyl having 2 to 18 carbon atoms, aralkyl having 7 to 18 carbon atoms;

$R_2$ is a member selected from straight and branched chain alkylene having 2 to 18 carbon atoms, cycloalkylene having 5 to 18 carbon atoms, arylene having 6 to 18 carbon atoms, aralkylene having 7 to 18 carbon atoms;

$R_3$ is a piperidine radical of formula (II);

$R_4$ is a member selected from straight and branched chain akylene having 2 to 18 carbon atoms, cycloalkylene having 5 to 18 carbon atoms, arylene having 6 to 18 carbon atoms, aralkylene having 7 to 18 carbon atoms;

$x$ is either 0 or 1;

$y$ is an integer from 2 to 200;

A and B each represent a terminal group with A being H and B being

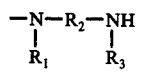

3. The compound according to claim 2, in which $R_5$, $R_6$, $R_8$ and $R_9$ are the same and are methyl groups.

4. The compound according to claim 2, in which $R_7$ is a member selected from hydrogen and alkyl having 1 to 6 inclusive carbon atoms.

5. The compound according to claim 4, in which $R_1$ is hydrogen and $R_3$ is the piperidine radical of formula (II).

6. The compound according to claim 4, in which $R_1$ and $R_3$ are identical and each of them is the piperidine radical of formula (II).

7. The compound according to claim 2, in which $x$ is 0, $R_1$ is a member selected from hydrogen and the piperidine radical of formula (II), $R_2$ is alkylene having 2 to 6 inclusive carbon atoms, $R_3$ is the piperidine radical of formula (II), $R_5$, $R_6$, $R_8$ and $R_9$ are each a methyl group, $R_7$ is a member selected from hydrogen and methyl, A is hydrogen, B is the group

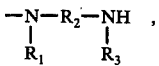

$y$ is an integer from 2 to 100.

8. A compound according to claim 2, in which $x$ is one, $R_1$ a member selected from hydrogen and the piperidine radical of formula (II), $R_2$ is alkylene having 2 to 6 inclusive carbon atoms, $R_3$ is the piperidine radical of formula (II), $R_4$ is a member selected from straight and branched chain alkylene having 6 to 10 carbon atoms, m-toluylene, substituted cycloalkylene derived from isophoronediisocyanate, $R_5$, $R_6$, $R_8$ and $R_9$ are methyl, $R_7$ is a member selected from hydrogen and methyl, A is hydrogen, B is the group

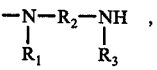

$y$ is an integer from 2 to 100.

9. A compound according to claim 1, in which a proportion of the $y$ units and the terminal group

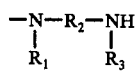

has the radical

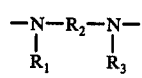

replaced by the radical selected from

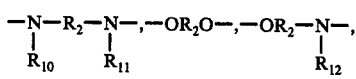

wherein $R_{10}$, $R_{11}$, $R_{12}$ are similar or different and each of them is individually a member selected from hydrogen, straight and branched chain alkyl having 1 to 18 carbon atoms, cycloalkyl having 5 to 18 carbon atoms, aryl having 6 to 18 carbon atoms, aralkyl having 7 to 18 carbon atoms, or $R_{10}$ and $R_{11}$ are linked together so that the group

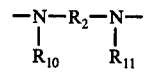

forms a heterocyclic ring having 6 to 8 inclusive members, which contains 2 nitrogen atoms; said proportion of the $y$ units with a replaced radical resulting from using, in the reaction for producing said compound, not over 2 moles of an amine or hydroxyl reactant containing the replacing radicals

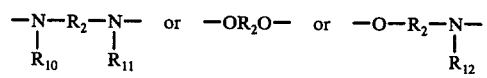

per one mole of the amine reactant containing the radical

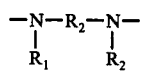

employed in the reaction.

10. A compound according to claim 9, in which $R_{10}$, $R_{11}$, $R_{12}$ are hydrogen.

11. A compound according to claim 10, in which $x$ is 0, $R_1$ is selected from hydrogen and the piperidine radical of formula (II), $R_2$ is alkylene having 2 to 6 inclusive carbon atoms, $R_3$ is the piperidine radical of formula (II), $R_5$, $R_6$, $R_8$ and $R_9$ are methyl groups, $R_7$ is selected from hydrogen and methyl, A is hydrogen, $y$ is an integer from 2 to 100.

12. A compound according to claim 10, in which $x$ is 1, $R_1$ is selected from hydrogen and the piperidine radical of formula (II), $R_2$ is alkylene having 2 to 6 carbon atoms, $R_4$ is a member selected from straight and branched chain alkylene having 6 to 10 carbon atoms, m-toluylene, substituted cycloalkylene derived from isophoronediisocyanate, $R_5$, $R_6$, $R_8$ and $R_9$ are individually methyl, $R_7$ is selected from hydrogen and methyl, A is hydrogen, $y$ is an integer from 2 to 100.

13. A compound according to claim 9 wherein not over 1 mole of replacing radical

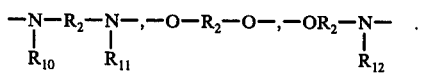

is used per mole of amine reactant containing the radical

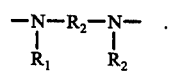

14. A synthetic polymer composition of increased light stability having incorporated with the polymer an amount of a compound according to claim 1 effective to increase the light stability of the polymer.

15. A composition according to claim 14 wherein the compound is (1).

16. A composition according to claim 14 wherein the compound is (2).

17. A composition according to claim 14, wherein said synthetic polymer is a polyolefin.

18. A composition according to claim 17, wherein said synthetic polymer is polypropylene.

19. A composition according to claim 17, wherein said synthetic polymer is polyethylene.

20. A composition according to claim 17, wherein said synthetic polymer is in the form of fibers.

21. A composition according to claim 4, wherein said compound is added to the synthetic polymer composition in an amount from 0.1 to 1% by weight referred to the synthetic polymer composition.

22. A composition according to claim 14 wherein said compound is added to the synthetic polymer composition in an amount of 0.01 to 5% by weight of the polymer.

23. A method of preparing a compound according to claim 1 comprising reacting either a diamine having the formula

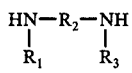

with a reactant selected from the group consisting of carbonyl chloride and $OCN-R_4-NCO$ in an inert solvent, in a molar ratio of diamine to said reactant ranging from 1:1 to 1.5:1 at a temperature sufficient to form the compound having the formula

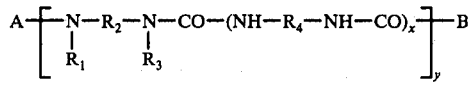

or employing a corresponding mixture of the diamine

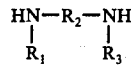

with not over 2 moles per mole of said diamine of a compound selected from the group consisting of

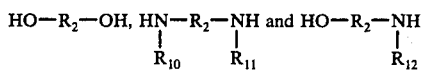

to form the compound

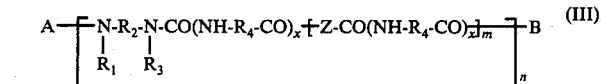

where Z represents a radical

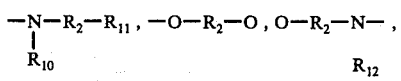

$m$ is a number from 0 to 2 and $n = y/(1+m)$.

* * * * *